United States Patent [19]
Hutchins

[11] 4,025,198
[45] May 24, 1977

[54] OPPOSITE-SIDES OBJECT INSPECTION SYSTEM

[76] Inventor: Thomas B. Hutchins, 310 N.W. Brynwood Lane, Portland, Oreg. 97229

[22] Filed: Mar. 17, 1976

[21] Appl. No.: 667,650

[52] U.S. Cl. .................................. 356/163; 353/28; 356/199; 356/237
[51] Int. Cl.² ......................................... G01B 11/00
[58] Field of Search ............ 353/28; 356/163, 199, 356/200, 237; 250/571, 572

[56] References Cited
UNITED STATES PATENTS

| | | |
|---|---|---|
| 3,776,643 | 12/1973 | Titoff .................................. 356/163 |
| 3,836,261 | 9/1974 | Clarke ................................ 356/163 |
| 3,964,191 | 6/1976 | Sieber et al. ...................... 356/163 |

Primary Examiner—John K. Corbin
Assistant Examiner—Richard A. Rosenberger
Attorney, Agent, or Firm—Kolisch, Hartwell, Dickinson & Stuart

[57] ABSTRACT

An inspection system including apparatus for projecting onto a portion of one side of an object in a viewing station a positionally aligned, unidirectionally reversed image of the corresponding portion of the opposite side of the object. The system is especially useful in noting from one side of an object the total lateral span of a defect, such as a knot in a piece of lumber, which may extend completely through the object.

4 Claims, 7 Drawing Figures

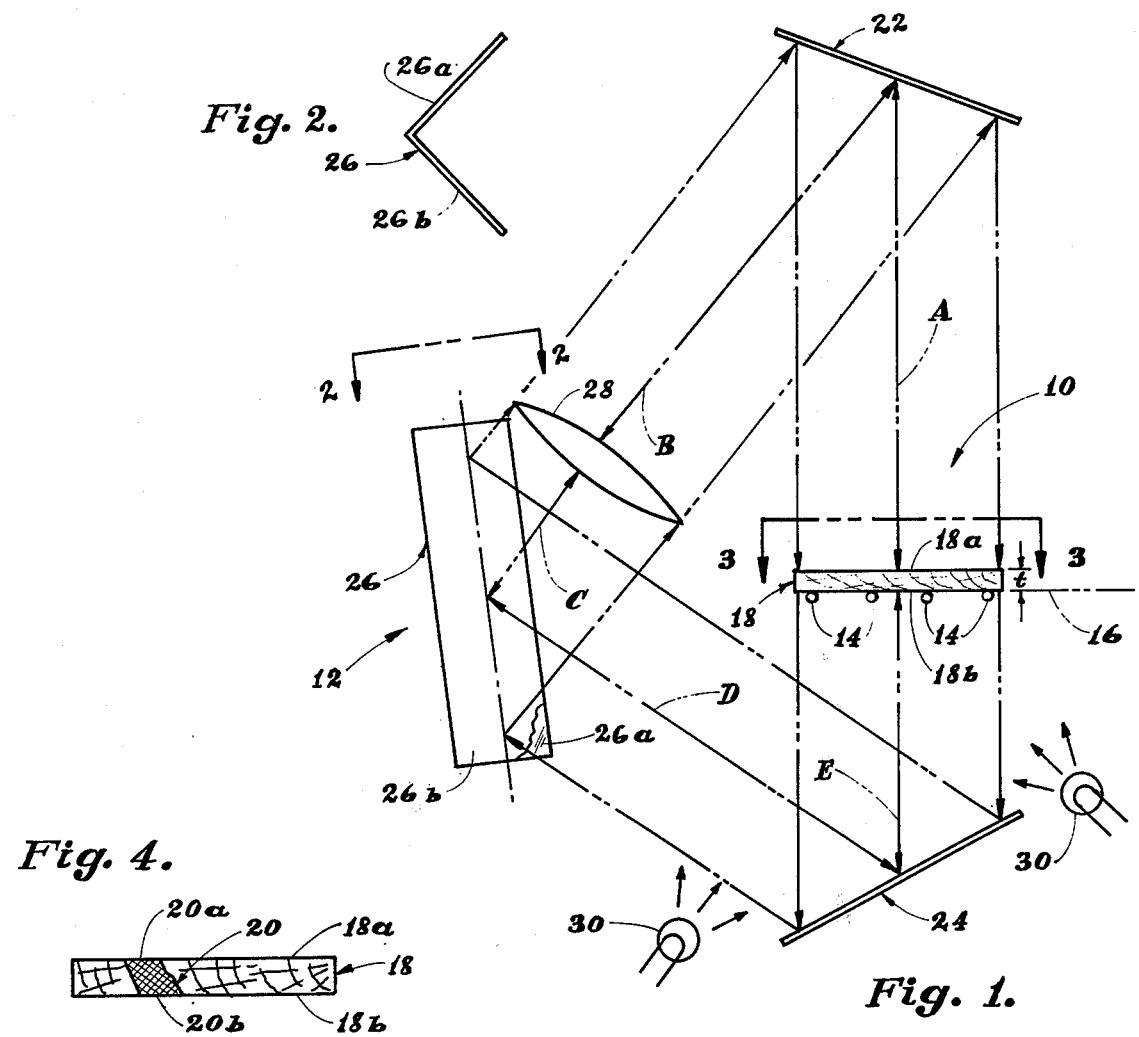
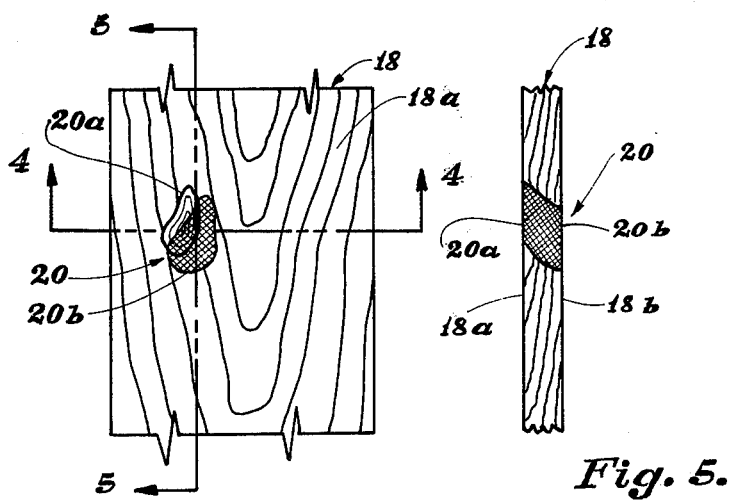
Fig. 2.
Fig. 4.
Fig. 3.
Fig. 5.
Fig. 1.

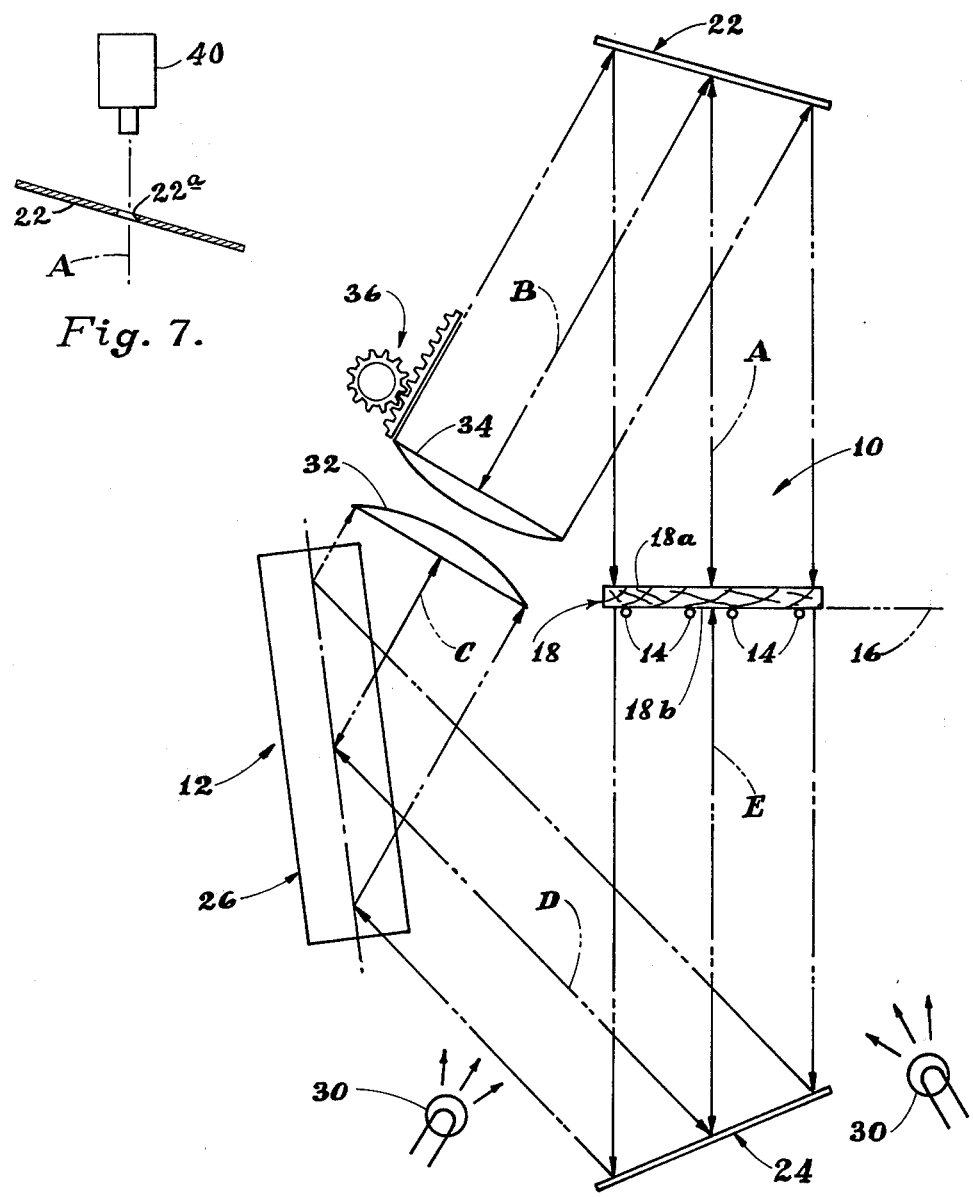

OPPOSITE-SIDES OBJECT INSPECTION SYSTEM

BACKGROUND AND SUMMARY OF THE INVENTION

This invention pertains to an object inspection system, and more particularly to such a system which enables the simple simultaneous inspection of the condition of opposite sides of a selected object.

There are various types of operations wherein it is necessary to inspect the opposite sides of an object in order to make a proper judgment as how next best to process the object. For example, in the manufacture of furniture, it is necessary to inspect the opposite sides of lumber pieces to determine the total lateral spreads of knots and other defects in such pieces so as to be able to determine how best to cut the lumber, with minimum waste, into the finally desired furniture piece shapes. Heretofore, it has been necessary first to inspect one side of such a lumber piece, and then to turn the piece over, usually manually, to examine the corresponding opposite side of the piece, thus to gauge the overall spread of a defect in the piece. Such a practice is obviously quite time consuming and expensive.

A general object of the present invention is to provide a unique inspection system for inspecting the opposite sides of an object, such as a piece of lumber, which system avoids in a practical and satisfactory manner the above-mentioned deficiencies of conventional inspection techniques.

More particularly, an object of the invention is to provide such a system which enables the ready and simple simultaneous inspection of opposite sides of an object, thus to enable instantaneous noting of the total lateral spread of a defect, such as a knot, in the object.

According to a preferred embodiment of the invention, an inspection system is proposed including apparatus for projecting onto a selected portion of one side of an object in a viewing station a positionally aligned, unidirectionally reversed image of the corresponding portion of the opposite side of the object. Such apparatus employs a pair of viewing and projection mirrors which are arranged to confront such opposite sides of an object in the station, with these two mirrors cooperating with an image-reversing mirror which is located outside the viewing station. In one embodiment of the invention, a single imaging lens is employed in the optical path which extends between the two viewing and projection mirrors. In a modification, a pair of such lens are used, these to lenses being coaxial and relatively adjustable to change the spacing therebetween. As will be explained, this modification enables adjustment of the apparatus properly to handle objects of different thicknesses.

With an object which is to be inspected in the viewing station, one side of the object is lighted, and the apparatus of the invention then projects a full-scale image of this side onto the other side of the object where it may be viewed simultaneously with such other side. The image-reversing mirror assures proper orientation of the projected image.

With such projection, it will be obvious that it is an extremely simple matter for an operator to view a single side of an object onto which has been projected the image of the opposite side, and to see clearly the total lateral extent of any defect, such as a knot, which may extend completely through the object.

It will further be appreciated that the proposed system, in both of its embodiments, as generally outlined above, is extremely simple in construction, can easily be used, and can readily be incorporated in various kinds of equipment.

These and other objects and advantages which are attained by the invention will become more fully apparent as the description thereof which now follows is read in conjunction with the accompanying drawings.

DESCRIPTION OF THE DRAWINGS

FIG. 1 is a simplified schematic view illustrating an inspection system constructed in accordance with the present invention.

FIGS. 2 and 3 are fragmentary views taken generally along the lines 2—2 and 3—3, respectively, in FIG. 1.

FIGS. 4 and 5 are fragmentary cross-sectional views taken generally along the lines 4—4 and 5—5, respectively, in FIG. 3.

FIG. 6 is a view similar to FIG. 1 showing a modification of the system of the invention.

FIG. 7 shows another modification of the system of the invention.

DETAILED DESCRIPTION OF THE INVENTION

Turning now to the drawings, and referring initially to FIGS. 1–5, inclusive, indicated generally at 10 is a viewing station for the inspection of lumber which is to be used in the manufacture of furniture. An inspection system which is intended to be used in conjunction with station 10, and which is constructed in accordance with the present invention, is indicated generally at 12.

Provided in station 10 for supporting various lumber pieces which are to be inspected are a plurality of elongated, spaced-apart, substantially parallel wires 14 which extend normal to the plane of FIG. 1. Four such wires are shown in station 10—these wires herein having a diameter of about 1/16th of an inch, and being spaced apart by about 5 inches. Such wires may stretch over any selected span (normal to the plane of FIG. 1) to define the length of a viewing station, and herein extend over a length of about 6 feet. In other words, the wires, whose opposite ends may be attached to any suitable structure, define a relatively optically open support surface for supporting a piece of lumber which is to be inspected. As can be seen, wires 14 are at a common elevation, and are adapted to support a piece of lumber at the elevation of the plane indicated at 16.

Shown in station 10 supported on wires 14 is a board 18 having a width herein of about 16 inches, and a thickness $t$. Board 18 has been placed in station 10 for the purpose of inspecting its upper and lower sides 18$a$, 18$b$, respectively, for the presence of knots or other defects which may be present in the board. With reference particulary to FIGS. 3–5, inclusive, a knot in board 18 is indicated generally at 20.

Included within system 12 are upper and lower viewing mirrors 22, 24, or optical reflectors, respectively, an image-reversing mirror 26, and a lens 28. System 12 herein, using as it does, a single lens, is intended for handling boards all of which will have the same thickness, namely, the thickness indicated at $t$ in FIG. 1. A modification of the invention will later be described which is especially suited for handling boards of differing thicknesses.

Mirrors 22, 24 are plane mirrors whose respective planes are oriented normal to the plane of FIG. 1, and whose viewing surfaces generally face station 10. Each of these mirrors is preferably located several feet away from previously mentioned plane 16. The exact way in which the mirrors should be positioned will be explained shortly. Each of these mirrors has a substantially square outline, with dimensions of about twenty inches by twenty inches. Mirror 22, the upper viewing mirror, is disposed at an angle of about 15° with respect to the horizontal. As can be seen, this mirror slopes upwardly and to the left at this angle in FIG. 1. Lower mirror 24 slopes upwardly and to the right in FIG. 1 at an angle of about 22½° to the horizontal.

As can be seen by studying FIGS. 1 and 2, image-reversing mirror 26 is made up of a pair of right-angularly disposed contiguous plane mirror plates 26a, 26b. The line of joinder between plates 26a, 26b lies in a plane parallel to the plane of FIG. 1, which plane intersects the mid-points of mirrors 22, 24 (as such are measured in a direction normal to the plane of FIG. 1). Further, plates 26a, 26b diverge in opposite directions, and at equal angles with respect to the plane just mentioned which is parallel to the plane of FIG 1. Each of plates 26a, 26b herein has a length of about 18 inches, and a width of about 10 inches. As viewed in FIG. 1, mirror 26 is tilted upwardly and to the left at an angle of about 7½° to the horizontal. It will be noted that mirror 26 is located below the level of station 10. The reason for this will be explained shortly.

It is important, for proper functioning of system 12, that the optical center of lens 28 be located centrally along the optical path which is defined by mirrors 22, 24, 26 between the opposite sides of a board in station 10 having the thickness $t$. The distance along this path from lens 28 to the top surface of such a board is equal to the sum of the distances designated A and B in FIG. 1. The distance from the center of the lens to the lower face of board 18 is equal to the sum of the distances indicated by the lines designated D, C and E in FIG. 1. It will thus be evident that it is necessary for mirror 26 to be offset from the center of the system so as to accommodate proper positioning of lens 28. Simply as a matter of choice herein, mirror 26 has been offset below mirror 28, and hence below station 10.

The focal length of lens 28, $f_L$, is defined by the following equation:

$$\frac{1}{f_L} = \frac{1}{A+B} + \frac{1}{C+D+E}$$

where: A, B, C, D and E are the distances indicated in FIG. 1. Lens 28 herein has a diameter of about 8 inches.

The specific means which are used to mount mirrors 22, 24, 26 and lens 28 in place form no part of the present invention, it being understood that any suitable means may be used for this purpose.

Completing a description of what is shown in FIG. 1, indicated generally at 30 is a lamp which is used to light up the bottom side of a board in station 10.

Referring again particularly to FIGS. 3, 4 and 5, it will be noted that the dimensions of knot 20 are different at different locations within board 18, and further that the knot extends at an oblique angle through the board. Such is the case with most knots, and in addition, it is common for the cross-sectional configuration of the knot to vary from location to location. Thus, referring to FIG. 4, it will be noted that the upper surface of knot 20, shown at 20a, is positioned somewhat to the left of the lower surface 20b of the knot as depicted in this figure. As can be seen in FIG. 5, upper surface 20a is located somewhat above lower surface 20b. Obviously, this characteristic of the knot would not be evident to a viewer looking at one side only of board 18. However, knowledge of the total lateral expanse of the knot through the board is important to assure proper cutting of the board so as to eliminate the knot.

As was mentioned earlier, in the past it has been necessary for an inspector physically to look first at one side of a board and then at the other, making appropriate marks on the board, so as to make a decision where and how to cut the board. With system 12, this kind of time-consuming and costly operation is not necessary. Considering how system 12 specifically performs, with board 18 positioned as described in station 10, and with lamp 30 lit, mirrors 22, 24, 26, in conjunction with lens 28, project onto the top side of the board a properly positioned and properly oriented image of the bottom surface of the board. This is illustrated in FIG. 3 where the top surface of knot 20, i.e., surface 20a, is shown along with the projected image of the bottom surface 20b of the knot. As a consequence, it is an extremely simple matter for an inspector to see instantaneously, and without having to turn the board over, the total lateral spread or extent of the defect, such as a knot. Thus, the system enables him rapidly to make a decision as how best to cut a board.

With the system arranged so that the distance A + B equals the distance C + D + E, the projected image is of the proper size. Mirror 26, it will be noted, unidirectionally reverses the image which it reflects, and this situation results in the projected image having a proper orientation. In other words, to the viewer it appears as if he is seeing through the top of the board in proper scale to the bottom side.

Considering FIG. 6 which illustrates a modification of the system, here the only difference from what is shown in FIG. 1, is that single lens 28 has been replaced by a pair of coaxial plano-convex lenses 32, 34, with lens 32 being fixed in place and lens 34 being movable axially toward and away from lens 32 through a rack and pinion mechanism shown at 36. All other things being the same in system 12, the focal length of each of lenses 32, 34, is twice the focal length of lens 28.

The modification just described in FIG. 6 enables system 12 to accommodate boards of different thickness. By this is meant the capability of the system to project onto the top surface of a board a properly sized and located image of the immediate underside of the board. The object of this modification is to enable the system to maintain the sum of the distances indicated at A and B substantially constant. Thus, the thicker the board that is placed in the viewing station, the closer lens 34 must be to lens 32, and vice versa. Rack and pinion mechanism 36 is used to effect adjustment of lens 34, and this mechanism may, of course, be calibrated so that an operator can directly set in the known thickness of whatever board is to be inspected.

FIG. 7 shows a modification, which is usable in both of the systems heretofore described, wherein mirror 22 is provided with a central aperture 22a, above which aperture is suitably mounted a conventional electronic optical scanner 40. Scanner 40 is oriented to view downwardly along previously mentioned path A which extends vertically herein. Scanner 40 is thus in a position to view simultaneously both the top side of a board in station 10, as well as the projected reverse side image. The scanner may be connected in the usual way to a computer for the storage of information for later use, or to a viewing terminal, such as a television-type monitor.

It should be understood, that while scanner 40 has been shown as working with an aperture in mirror 22, it could also be used in conjunction with similar apertures provided in either of mirrors 24, 26.

Further it is possible to use such a scanner which is offset from a mirror, so that it does not necessarily work in cooperation with an aperture in the mirror.

While the modifications of the system of the invention that have been described herein have been disclosed as having the limited width (measured normal to the plane of FIG. 1) of about 20 inches, an obvious further modification in the system would be to use a plurality of side-by-side closely juxtaposed arrangements like those shown in FIGS. 1 and 6, so as to enable simultaneous viewing of a considerably longer length of a board.

In all modifications, the system is bidirectional. In other words, either side of an object could be illuminated for projection onto the opposite side. It should be noted that the dash-double-dot lines extending from mirror to mirror in FIGS. 1 and 6 have been included simply to represent the boundaries, in the planes of these figures, of the light rays extending between the opposite sides of board 18 in station 10.

It will further be noted that the angular orientations of the mirrors may be changed in accordance with well known optical principles to accommodate different positions for mirror 26.

Thus, while several modifications of the invention have been described and illustrated herein, it is appreciated that other variations and modifications may be made without departing from the spirit of the invention.

It is claimed and desired to secure by Letters Patent:

1. Apparatus for projecting onto a portion of one side of an object in a viewing station a positionally aligned, unidirectionally reversed image of the corresponding portion of the opposite side of the object, said apparatus comprising
    means defining a path for the bidirectional transmission of optical energy between such opposite-side corresponding portions of an object in said viewing station, and
    image-reversing means positioned along said path between the path's ends for unidirectionally reversing and projecting toward one of said ends any image viewed at the opposite end, and vice versa.

2. The apparatus of claim 1, wherein said path-defining means includes a pair of spaced, axially aligned lens means, and which further includes means operatively associatedwith said lens means to produce selected relative movement therebetween to change the spacing thereof, thus to accommodate objects of different thicknesses in said station.

3. Apparatus for projecting onto a portion of one side of an object in a viewing station a positionally aligned, unidirectionally reversed image of the corresponding portion of the opposite side of the object, said apparatus comprising
    a first optical reflector disposed on one side of said station for reflecting along one path portion an image of one side of an object in the station, and further for reflecting onto said one side of such an object an image received by the first reflector along said one path portion,
    a second optical relector disposed on the opposite side of said station for reflecting along another path portion an image of the opposite side of an object in the station, and further for reflecting onto said opposite side of such an object an image received by the second reflector along said other path portion,
    said one and other path portions converging in a region, and
    image-reversing means located in said region for unidirectionally reversing and projecting along said one path portion an image received by the image-reversing means along said other path portion, and vice versa.

4. The apparatus of claim 3 which further includes a pair of spaced axially aligned lens means disposed in at least one of said path portions, and means operatively associated with said lens means to produce selected relative movement therebetween to change the spacing thereof, thus to accommodate objects of different thicknesses in said station.

* * * * *

UNITED STATES PATENT AND TRADEMARK OFFICE
CERTIFICATE OF CORRECTION

PATENT NO. : 4,025,198
DATED : May 24, 1977
INVENTOR(S) : Thomas B. Hutchins

It is certified that error appears in the above-identified patent and that said Letters Patent are hereby corrected as shown below:

In Col. 1, line 51, change "to" to --two--.

Signed and Sealed this

Fourth Day of April 1978

[SEAL]

Attest:

RUTH C. MASON
Attesting Officer

LUTRELLE F. PARKER
Acting Commissioner of Patents and Trademarks